United States Patent
Chachad et al.

(10) Patent No.: US 11,580,024 B2
(45) Date of Patent: Feb. 14, 2023

(54) MEMORY PIPELINE CONTROL IN A HIERARCHICAL MEMORY SYSTEM

(71) Applicant: Texas Instruments Incorporated, Dallas, TX (US)

(72) Inventors: Abhijeet Ashok Chachad, Plano, TX (US); Timothy David Anderson, University Park, TX (US); Kai Chirca, Dallas, TX (US); David Matthew Thompson, Dallas, TX (US)

(73) Assignee: Texas Instruments Incorporated, Dallas, TX (US)

( * ) Notice: Subject to any disclaimer, the term of this patent is extended or adjusted under 35 U.S.C. 154(b) by 0 days.

(21) Appl. No.: 17/492,776

(22) Filed: Oct. 4, 2021

(65) Prior Publication Data

US 2022/0027275 A1    Jan. 27, 2022

Related U.S. Application Data

(63) Continuation of application No. 16/879,264, filed on May 20, 2020, now Pat. No. 11,138,117.
(Continued)

(51) Int. Cl.
*G06F 12/00* (2006.01)
*G06F 12/0842* (2016.01)
(Continued)

(52) U.S. Cl.
CPC .......... *G06F 12/0842* (2013.01); *G06F 1/14* (2013.01); *G06F 9/544* (2013.01);
(Continued)

(58) Field of Classification Search
CPC .......... G06F 12/0842; G06F 12/0811; G06F 12/0888; G06F 1/14; G06F 9/38;
(Continued)

(56) References Cited

U.S. PATENT DOCUMENTS 6,161,208 A * 12/2000 Dutton ................ G06F 11/1064
714/E11.037
9,223,710 B2  12/2015 Alameldeen et al.
(Continued)

OTHER PUBLICATIONS

International Search Report for PCT/US2020/034498 dated Aug. 13, 2020.
(Continued)

*Primary Examiner* — Shawn X Gu
(74) *Attorney, Agent, or Firm* — Brian D. Graham; Frank D. Cimino

(57) ABSTRACT

In described examples, a processor system includes a processor core generating memory transactions, a lower level cache memory with a lower memory controller, and a higher level cache memory with a higher memory controller having a memory pipeline. The higher memory controller is connected to the lower memory controller by a bypass path that skips the memory pipeline. The higher memory controller: determines whether a memory transaction is a bypass write, which is a memory write request indicated not to result in a corresponding write being directed to the higher level cache memory; if the memory transaction is determined a bypass write, determines whether a memory transaction that prevents passing is in the memory pipeline; and if no transaction that prevents passing is determined to be in the memory pipeline, sends the memory transaction to the lower memory controller using the bypass path.

20 Claims, 4 Drawing Sheets

Related U.S. Application Data

(60) Provisional application No. 62/852,480, filed on May 24, 2019.

(51) Int. Cl.
*G06F 12/0811* (2016.01)
*G06F 12/0888* (2016.01)
*G06F 1/14* (2006.01)
*G06F 9/54* (2006.01)

(52) U.S. Cl.
CPC ...... *G06F 12/0811* (2013.01); *G06F 12/0888* (2013.01); *G06F 2212/1016* (2013.01)

(58) Field of Classification Search
CPC ...... G06F 9/382; G06F 9/3826; G06F 9/3828; G06F 9/3836; G06F 9/3867; G06F 9/544; G06F 9/30079; G06F 2212/1016
See application file for complete search history.

(56) References Cited

U.S. PATENT DOCUMENTS

| | | |
|---|---|---|
| 10,073,778 B1 | 9/2018 | Agarwal et al. |
| 2010/0100683 A1 | 4/2010 | Guthrie et al. |
| 2012/0191913 A1 | 7/2012 | Damodaran et al. |
| 2012/0260031 A1 | 10/2012 | Chachad et al. |
| 2013/0036337 A1 | 2/2013 | Venkatasubramanian et al. |
| 2015/0178204 A1 | 6/2015 | Ray et al. |

OTHER PUBLICATIONS

International Search Report for PCT/US2020/034507 dated Aug. 20, 2020.

* cited by examiner

MEMORY PIPELINE CONTROL IN A HIERARCHICAL MEMORY SYSTEM

CROSS-REFERENCE TO RELATED APPLICATION

This application is a continuation of U.S. patent application Ser. No. 16/879,264, filed May 20, 2020, which claims the benefit of and priority to U.S. Provisional Patent Application No. 62/852,480, filed May 24, 2019, each of which is fully incorporated herein by reference.

TECHNICAL FIELD

The present disclosure relates generally to a processing device that can be formed as part of an integrated circuit, such as a system on a chip (SoC). More specifically, this disclosure relates to such a system with improved management of write operations.

BACKGROUND

An SOC is an integrated circuit with multiple functional blocks (such as one or more processor cores, memory, and input and output) on a single die.

Hierarchical memory moves data and instructions between memory blocks with different read/write response times for respective processor cores, such as a central processing unit (CPU) or a digital signal processor (DSP). For example, memories which are more local to respective processor cores will typically have lower response times. Hierarchical memories include cache memory systems with multiple levels (such as L1 and L2), in which different levels describe different degrees of locality or different average response times of the cache memories to respective processor cores. Herein, the more local or lower response time cache memory (such as an L1 cache) is referred to as being a higher level cache memory than a less local or higher response time lower level cache memory (such as an L2 cache or L3 cache). Associativity of a cache refers to the cache storage segregation, where set associativity divides the cache into a number of storage sets and each such set stores a number (the way) of blocks, while a fully associative cache is unconstrained by a set limitation. Accordingly, for an integer N, each location in main memory (system memory) can reside in any one of N possible locations in an N-way associative cache.

A "victim cache" memory caches data (such as a cache line) that was evicted from a cache memory, such as an L1 cache. If an L1 cache read results in a miss (the data corresponding to a portion of main memory is not stored in the L1 cache), then a lookup occurs in the victim cache. If the victim cache lookup results in a hit (the data corresponding to the requested memory address is present in the victim cache), the contents of the victim cache location producing the hit, and the contents of a corresponding location in the respective cache (L1 cache in this example), are swapped. Some example victim caches are fully associative. Data corresponding to any location in main memory can be mapped to (stored in) any location in a fully associative cache.

SUMMARY

In described examples, a processor system includes a processor core generating memory transactions, a lower level cache memory with a lower memory controller, and a higher level cache memory with a higher memory controller having a memory pipeline. The higher memory controller is connected to the lower memory controller by a bypass path that skips the memory pipeline. The higher memory controller: determines whether a memory transaction is a bypass write, which is a memory write request indicated not to result in a corresponding write being directed to the higher level cache memory; if the memory transaction is determined a bypass write, determines whether a memory transaction that prevents passing is in the memory pipeline; and if no transaction that prevents passing is determined to be in the memory pipeline, sends the memory transaction to the lower memory controller using the bypass path.

DETAILED DESCRIPTION

Figure 1:
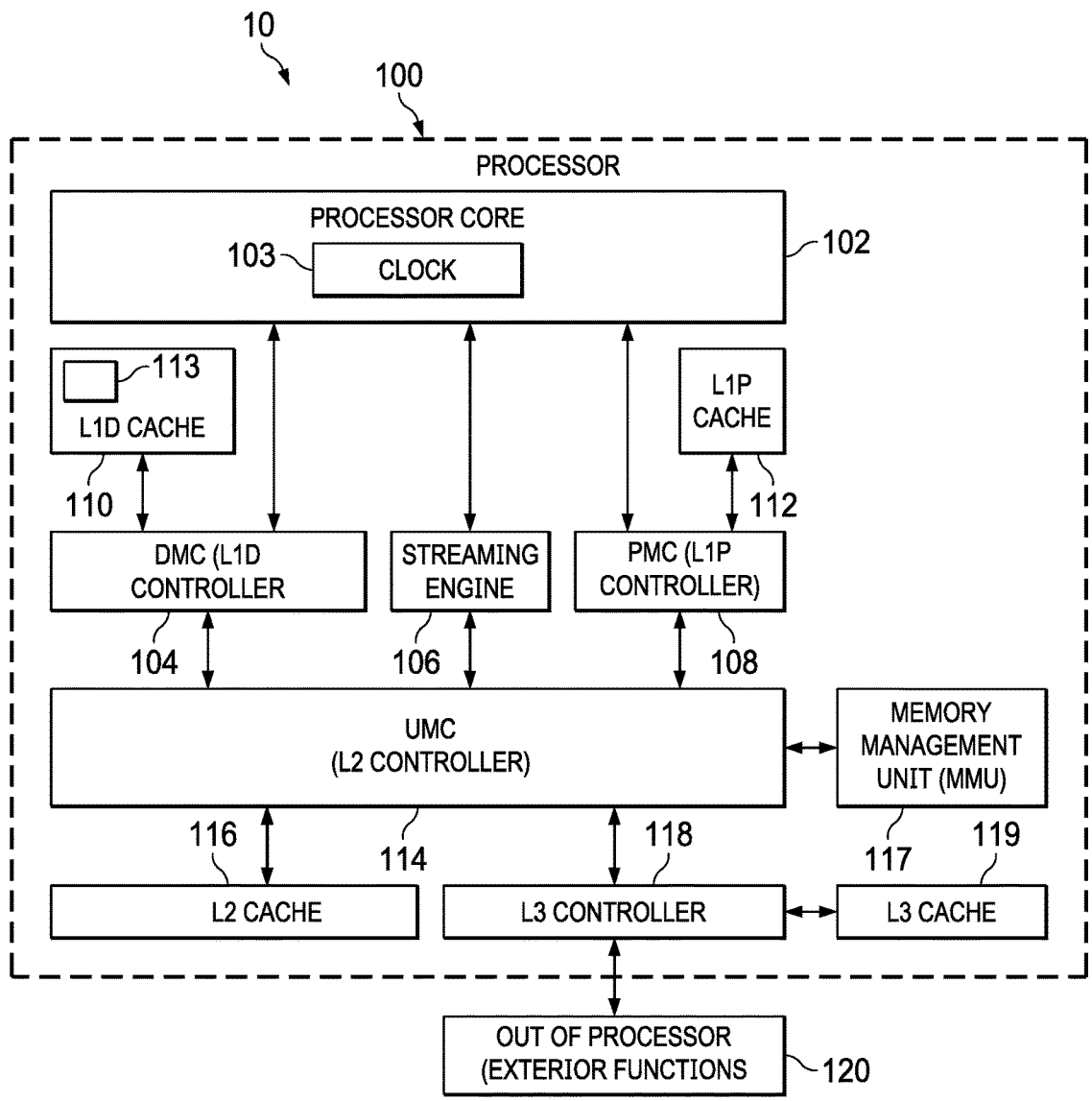
FIG. 1 is a block diagram of an example processor that is a portion of an SoC.

FIG. 1 is a block diagram of an example processor 100 that is a portion of an SoC 10. SoC 10 includes a processor core 102, such as a CPU or DSP, that generates new data. Processor 100 can include a clock 103, which can be part of processor core 102 or separate therefrom (separate clock not shown). Processor core 102 also generates memory read requests that request reads from, as well as memory write requests that request writes to, a data memory controller 104 (DMC) and a streaming engine 106. In some embodiments, processor core 102 generates one read request or write request per processor core clock cycle. Memory controllers return a write acknowledgment to processor core 102 to confirm that a requested memory write has been performed. Processor core 102 is also coupled to receive instructions from a program memory controller 108 (PMC). Streaming engine 106 facilitates processor core 102 sending certain memory transactions and other memory-related messages that bypass DMC 104 and PMC 108.

SoC 10 has a hierarchical memory system. Each cache at each level may be unified or divided into separate data and program caches. For example, the DMC 104 may be coupled to a level 1 data cache 110 (L1D cache) to control data writes to and data reads from the L1D cache 110. Similarly, the PMC 108 may be coupled to a level 1 program cache 112 (L1P cache) to read instructions for execution by processor core 102 from the L1P cache 112. (In this example, processor core 102 does not generate writes to L1P cache 112.) The L1D cache 110 can have an L1D victim cache 113. A unified memory controller 114 (UMC) for a level 2 cache (L2 cache 116, such as L2 SRAM) is communicatively coupled to receive read and write memory access requests from DMC 104 and PMC 108, and to receive read requests from streaming engine 106, PMC 108, and a memory management unit 117 (MMU). (The example L2 controller UMC 114 is called a "unified" memory controller in the example system because UMC 114 can store both instructions and data in L2 cache 116.) UMC 114 is communicatively coupled to pass read data and write acknowledgments (from beyond level 1 caching) to DMC 104, streaming engine 106, and PMC 108, which are then passed on to processor core 102. UMC 114 is also coupled to control writes to, and reads from, L2 cache 116, and to pass memory access requests to a level 3 cache controller 118 (L3 controller). L3 controller 118 is coupled to control writes to, and reads from, L3 cache 119. UMC 114 is coupled to receive write acknowledgments, and data, read from L2 cache 116 and L3 cache 119 (via L3 controller 118). UMC 114 is configured to control pipelining of memory transactions for program content and data content (read and write requests for instructions, data transmissions, and write acknowledgments). L3 controller 118 is coupled to control writes to, and reads from, L3 cache 119, and to mediate transactions with exterior functions 120 that are exterior to processor 100, such as other processor cores, peripheral functions of the SOC 10, and/or other SoCs (and also to control snoop transactions). That is, L3 controller 118 is a shared memory controller of the SoC 10, and L3 cache 119 is a shared cache memory of the SoC 10. Accordingly, memory transactions relating to processor 100 and exterior functions 120 pass through L3 controller 118.

Memory transactions are generated by processor core 102 and are communicated towards lower level cache memory, or are generated by exterior functions 120 and communicated towards higher level cache memory. For example, a victim write transaction may be originated by UMC 114 in response to a read transaction from the processor core 102 that produces a miss in L2 cache 116.

MMU 117 provides address translation and memory attribute information to the processor core 102. It does this by looking up information in tables that are stored in memory (connection between MMU 117 and UMC 114 enables MMU 117 to use read requests to access memory containing the tables).

Figure 2:
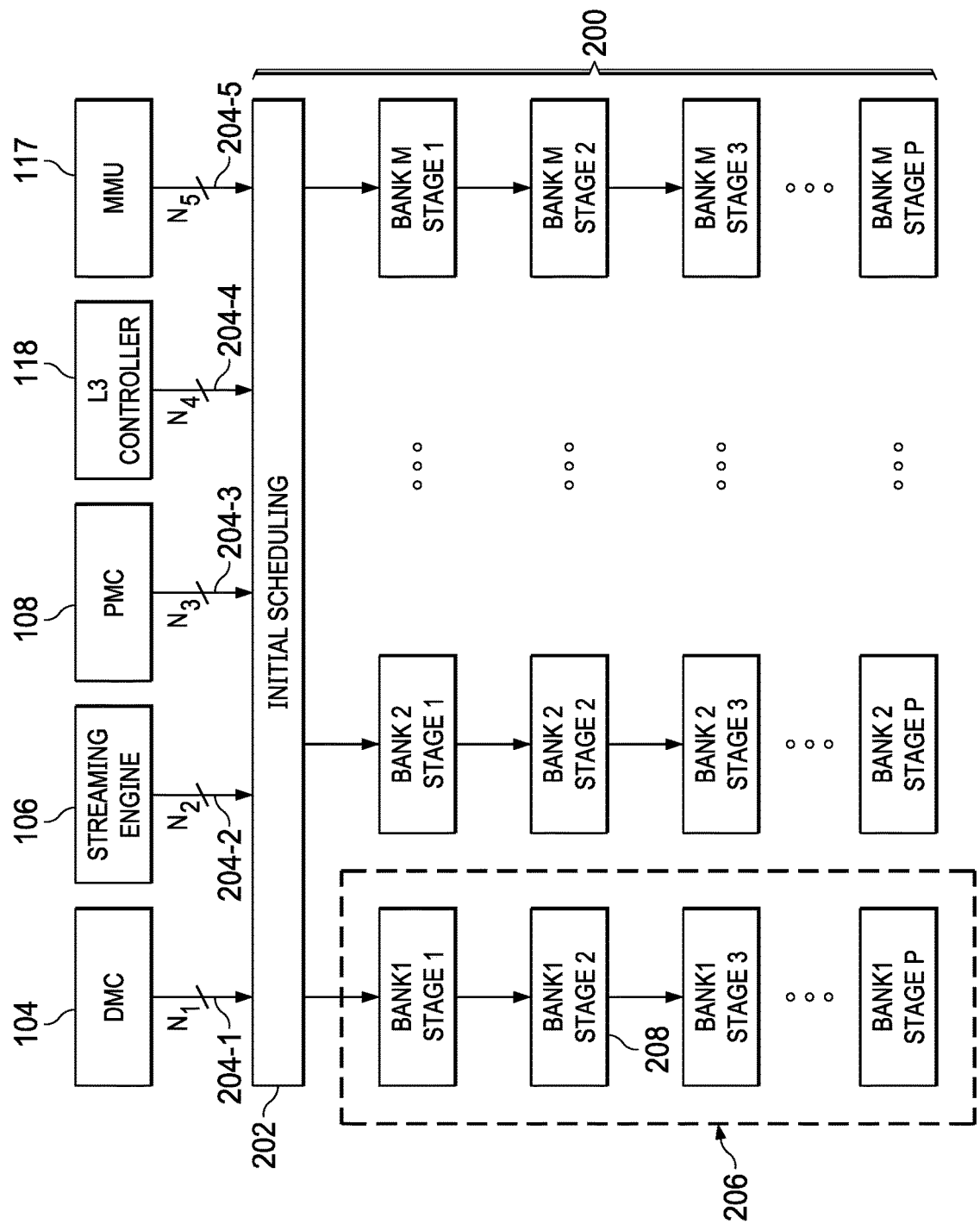
FIG. 2 is a block diagram of an example memory pipeline for the SoC of FIG. 1.

FIG. 2 is a block diagram of an example memory pipeline 200 included within or associated with the FIG. 1 UMC 114, so for illustration FIG. 2 also repeats various blocks from FIG. 1 that communicate with UMC 114. Memory pipeline 200 includes an initial scheduling block 202 coupled to an integer number M of pipeline banks 206. Each pipeline bank 206 includes an integer number P of stages 208 and is illustrated as a vertical column below initial scheduling block 202. DMC 104 is coupled to initial scheduling block 202 by a bus 204-1 that is a number $N_1$ lines wide, enabling DMC 104 to make a read or write request transferring a number $N_1$ bits of data at a time. Streaming engine 106 is coupled to initial scheduling block 202 by a bus 204-2 that is a number $N_2$ lines wide, enabling streaming engine 106 to make a read request transferring a number $N_2$ bits of data at a time. PMC 108 is coupled to initial scheduling block 202 by a bus 204-3 that is a number $N_3$ lines wide, enabling PMC 108 to make a read request transferring a number $N_3$ bits of data at a time. L3 controller 118 is coupled to initial scheduling block 202 by a bus 204-4 that is a number $N_4$ lines wide, enabling L3 118 to make a read or write request transferring a number $N_4$ bits of data at a time. MMU 117 is coupled to initial scheduling block 202 by a bus 204-5 that is a number $N_5$ lines wide, enabling MMU 117 to make a read request transferring a number $N_5$ bits of data at a time.

When a memory controller of processor 100 (such as DMC 104, streaming engine 106, PMC 108, MMU 117, or L3 controller 118) communicates to UMC 114 a request for a read from, or a write to, a memory intermediated by UMC 114 (such as L2 cache 116, L3 cache 119, or a memory in exterior functions 120), initial scheduling block 202 schedules the request to be handled by an appropriate pipeline bank 206 for the particular request. Accordingly, initial scheduling block 202 performs arbitration on read and write requests. Arbitration determines which pipeline bank 206 will receive which of the memory transactions queued at the initial scheduling block 202, and in what order. Typically, a read or write request is scheduled into a corresponding one of pipeline banks 206, depending on, for example, the memory address of the data being written or requested, request load of pipeline banks 206, or a pseudo-random function. Initial scheduling block 202 schedules read and write requests received from DMC 104, streaming engine 106, PMC 108, and L3 controller 118, by selecting among the first stages of pipeline banks 206. Memory transactions requested to be performed on L3 cache 119 (or exterior functions 120) are arbitrated and scheduled into an L3 cache pipeline by an L3 cache scheduling block 404 in L3 controller 118 (see FIG. 4) after passing through memory pipeline 200 corresponding to L2 cache 116 (pipeline banks 206, and potentially bus snooping-related stages, which are not shown).

Request scheduling prevents conflicts between read or write requests that are to be handled by the same pipeline bank 206, and preserves memory coherence (further discussed below). For example, request scheduling maintains order among memory transactions that are placed into a memory transaction queue (memory access request queue) of initial scheduling block 202 by different memory controllers of the processor 100, or by different bus lines of a same memory controller.

Further, a pipeline memory transaction (a read or write request) sent by DMC 104 or PMC 108 is requested because the memory transaction has already passed through a corresponding level 1 cache pipeline (in DMC 104 for L1D cache 110, and in PMC 108 for L1P cache 112), and is targeted to a lower level cache or memory endpoint (or exterior functions 120), or has produced a miss in the respective level 1 cache, or bypassed L1D cache 110 because a corresponding data payload of a write request is non-cacheable by L1D cache 110. Generally, memory transactions directed to DMC 104 or PMC 108 that produce level 1 cache hits result in a write acknowledgment from L1D cache 110 or a response with data or instructions read from L1D cache 110 or L1P cache 112, respectively. Accordingly, memory transactions that produce level 1 cache hits generally do not require access to the pipeline banks 206 shown in FIG. 2, which control or intermediate memory access to L2 cache 116, L3 cache 119, and exterior functions 120 (see FIG. 1).

Pipeline banks 206 shown in FIG. 2 are part of UMC 114. L1D cache 110 can hold data generated by processor core 102. Exterior functions 120 can access data in L1D cache 110 by, for example, writing the data to L2 cache 116 or L3 cache 119, or using snoop transactions controlled by L3 controller 119 and managed by UMC 114 (L2 controller, as a proxy) to read or evict the data from L1D cache 110.

Memory coherence is when contents (or at least contents deemed or indicated as valid) of the memory in a system are the same contents expected by the one or more processors in the system based on an ordered stream of read and write requests. Writes affecting a particular data, or a particular memory location, are prevented from bypassing earlier-issued writes or reads affecting the same data or the same memory location. Also, certain types of transactions take priority, such as victim cache transactions and snoop transactions.

Bus snooping is a scheme by which a coherence controller (snooper) in a cache monitors or snoops bus transactions to maintain memory coherence in distributed shared memory systems (such as in SoC 10). If a transaction modifying a shared cache block appears on a bus, the snoopers check whether their respective caches have the same copy of the shared block. If a cache has a copy of the shared block, the corresponding snooper performs an action to ensure memory coherence in the cache. This action can be, for example, flushing, invalidating, or updating the shared block, according to the transaction detected on the bus.

"Write streaming" refers to a device (e.g., processor core 102) issuing a stream of write requests, such as one write request per cycle, without stalls. Write streaming can be interrupted by stalls caused by, for example, a full buffer, or by running out of write request identifier numbers. The ability to cause write requests to be pulled from the memory transaction queue as quickly as possible promotes write streaming.

For processor core 102 to know that a write has completed, it must receive a write acknowledgement. To maintain coherence, processor core 102 may self-limit to a given number of outstanding write requests by throttling write requests that would exceed a limit until a write acknowledgement is received for an outstanding write request. Accordingly, processor core 102 and L1D cache 110 may wait on the write acknowledgment (or "handshake") to proceed, meanwhile stalling corresponding write streaming processes within the processor core 102. Stalls that interrupt write streaming can also be caused by the processor core 102 or DMC 104 waiting for a write acknowledgment from a previous write request. Processor core 102 can also be configured to stall while waiting for a write acknowledgment with respect to certain operations, such as fence operations. Write completion in a lower level cache, such as L2 cache 116 or L3 cache 119, can be detected by DMC 104 (the level 1 cache 110 controller) using a write acknowledgment (handshake) forwarded by UMC 114 (the level 2 cache 116 controller). However, writes can take many cycles to complete, due to various pipeline requirements including arbitration, ordering, and coherence.

At the first level of arbitration performed by initial scheduling block 202, UMC 114 (the L2 cache 116 controller, which includes initial scheduling block 202) determines whether to allow a memory transaction to proceed in memory pipeline 200, and in which pipeline bank 206 to proceed. Writes to L2 cache 116 typically have few operations between (1) initial arbitration and scheduling and (2) write completion. Remaining operations for a scheduled write request can include, for example, checking for errors (such as firewall, addressing, and out of range errors), a read-modify-write action (updating an error checking code of a write request's data payload), and committing to memory the write request's data payload. Generally, each pipeline bank 206 is independent, such that write transactions on pipeline banks 206 (for example, writes of data from L1D cache 110 to L2 cache 116) do not have ordering or coherence requirements with respect to write transactions on other pipeline banks 206. Within each pipeline bank, writes to L2 cache 116 proceed in the order they are scheduled. In the case of partial writes that spawn a read-modify-write transaction, relative ordering is maintained. If a memory transaction causes an addressing hazard or violates an ordering requirement, the transaction stalls and is not issued to a pipeline bank 206. (Partial writes are write requests with data payloads smaller than a destination cache memory's minimum write length. Partial writes trigger read-modify-write transactions, in which data is read from the destination cache memory to pad the write request's data payload to the destination cache memory's minimum write length, and an updated error correction code (ECC) is generated from and appended to the resulting padded data payload. The padded data payload, with updated ECC, is what is written to the destination cache memory.)

Due to these characteristics of the memory pipeline 200, once a write is scheduled within a pipeline bank 206 (for example, a write of data from L1D cache 110 to L2 cache 116), the write is guaranteed to follow all ordering requirements and not to violate coherence (accordingly, conditions to be satisfied to avoid breaking ordering and coherence are met). Committing the write to memory may take a (variable) number of cycles, but a read issued after this write was issued will "see" the write. Accordingly, if the read is requesting data or a memory location modified by the write, the read will retrieve the version of the data or the contents of the memory location specified by the write, and not a previous version. Write-write ordering is also maintained. L3 cache 119 write requests can also be scheduled by the memory pipeline 200 (by UMC 114) so that ordered completion of the L3 cache 119 write requests is guaranteed. These guarantees mean that write requests scheduled into a pipeline bank 206 by the memory pipeline 200 (the L2 cache pipeline) can be guaranteed to comply with ordering and coherence requirements, and to complete within a finite amount of time. Put differently, this guarantee is an assurance that a write transaction that is to a particular address and that is currently being scheduled onto a pipeline bank 206 will "commit" its value to memory (the write will complete and store a corresponding data payload in memory) after a previously scheduled write transaction to the same address, and before a later scheduled write transaction to the same address. This guarantee can be based on the pipeline being inherently "in-order," so that once a command enters the pipeline, it will be written to memory (commit) in the order it was scheduled. In other words, there are no bypass paths within the pipeline. (The bypass path described below is handled so that it does not break the ordering guarantee, for example, with respect to older transactions targeting a same memory address.)

"Contemporaneously with" is defined herein as meaning at the same time as, or directly after. Accordingly, a first event occurring "contemporaneously with" a second event can mean that the two events occur on the same cycle of a system clock.

UMC 114 (the L2 controller) sends the write acknowledgment for writes of data to L2 cache 116 or higher level cache (for example, of data from L1D cache 110) to DMC 104 (the L1 controller) contemporaneously with the corresponding write request being scheduled by initial scheduling block 202 (the first level of arbitration). Accordingly, the write acknowledgment indicating write completion is sent contemporaneously with the write request being scheduled, rather than after memory pipeline 200 finishes processing the write request. This accelerated acknowledgment is enabled by the guarantee that the scheduled write request will complete in order and in compliance with coherence requirements. UMC 114 gives the illusion that write requests are being completed on the cycle on which they are scheduled, rather than the cycle on which corresponding data is committed (written) to memory. From a perspective of observability of processor core 102 or DMC 104, it is as if L2 cache 116 instantly completed the write request when the write request was scheduled. This enables DMC 104 to un-stall processor core 102 more quickly (or prevent processor core 102 stalls), and enables write requests to be pulled from queue with lower latency (faster), improving overall performance. The queue is a queue of transactions in UMC 114 that are sent from respective "masters" (functional blocks that can send memory transactions to UMC 114 to be queued), such as DMC 104, streaming engine 106, PMC 108, MMU 117, and L3 controller 118. The queue can be implemented as holding stages where memory transactions reside while waiting to be arbitrated and scheduled into a pipeline bank 206 by initial scheduling block 202.

Processor core 102 generally is configured to read data from memory to work on the data. This is also true for other processor cores 102 of other processors (such as processors 100) of SoC 10, with respect to memory accessible by those other processors. However, other processors of SoC 10 require data generated by processor core 102 to be available outside the data-generating processor 100 to be able to access the generated data. This means the generated data passes through L3 controller 118 to be externally accessible, either within shared memory (L3 cache 119) or by transmission to exterior functions 120.

Figure 3:
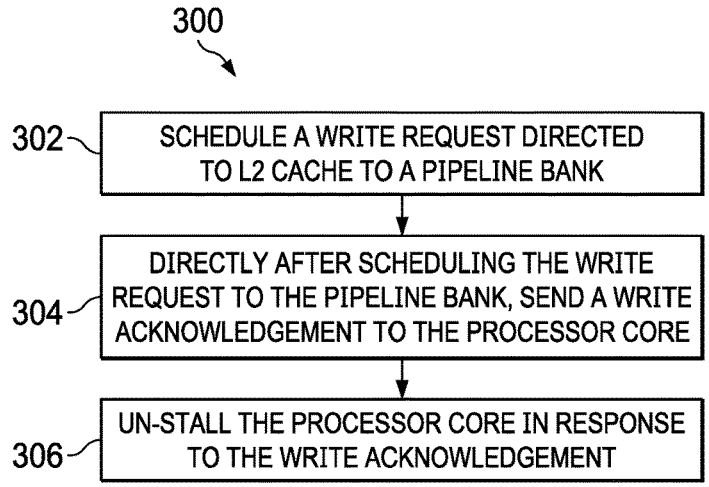
FIG. 3 is an example of a process for memory write operations for the SoC of FIG. 1.

FIG. 3 is an example of a process 300 for memory write operations for SoC 10 of FIG. 1. In step 302, initial scheduling block 202 schedules a write request, directed to L2 cache 116, to a pipeline bank 206. In step 304, directly after the write request is scheduled to the pipeline bank, UMC 114 (L2 cache controller) sends a write acknowledgment to processor core 102. In step 306, processor core 102 is un-stalled in response to the write acknowledgment.

Figure 4:
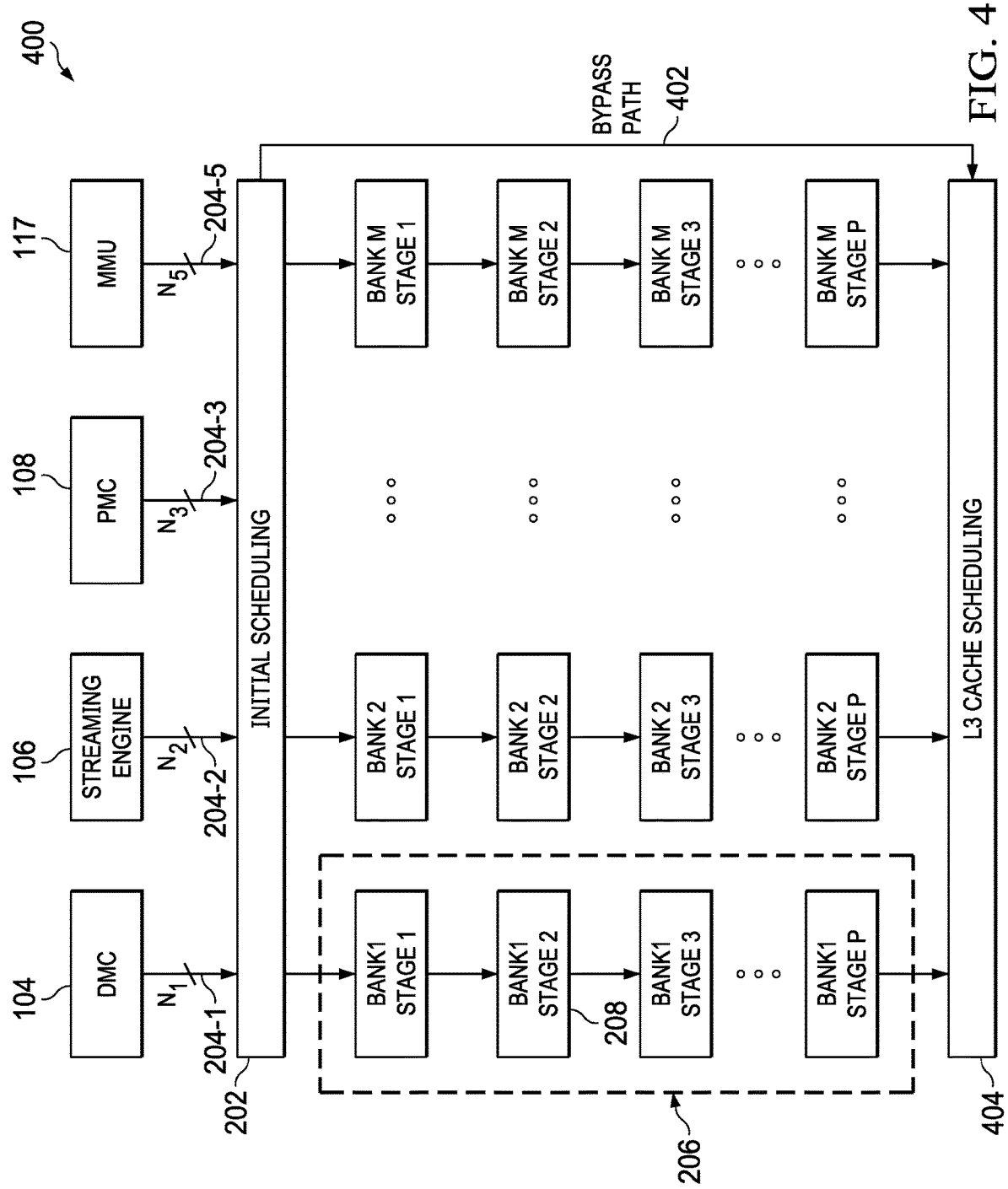
FIG. 4 is a block diagram of an example memory pipeline for the SoC of FIG. 1.

FIG. 4 is a block diagram of an example memory pipeline 400 for SoC 10 of FIG. 1. Memory pipeline 400 as shown in FIG. 4 is similar to a memory pipeline 200 as shown in FIG. 2, but also includes a bypass path 402. Bypass path 402 couples initial scheduling block 202 to L3 cache scheduling block 404, so memory pipeline corresponding to at least one level of cache is skipped. For example, bypass path 402 enables bypass writes to bypass portions of memory pipeline 400 related to L2 cache 116, shortening the total processing time for bypass writes. Accordingly, writes to certain memory regions can be written to L3 cache 119 without being written to L2 cache 116 (or other lower level cache). Such writes (bypass writes) can be safely performed without access to memory pipeline stages related to L2 cache 116, including pipeline banks 206 and related bus snooping (not shown). This simplifies coherence requirements for bypass writes.

Memory coherence imposes ordering requirements in order for bypass writes to be allowed to use bypass path 402. For example, writes may not bypass other writes (write-write ordering); writes may not bypass reads (read-write ordering); writes may not bypass victim cache transactions (for example, write requests from L1D victim cache 113 to L1D cache 110, which can be caused to be processed by UMC 114 by a cache miss of the victim cache-related write request at the L1 level); and writes may not bypass snoop responses (for example, snoop responses corresponding to a controller requesting a write from victim cache to L1D cache 110 when the request is not caused by a cache miss). Victim cache transactions and snoop responses are high priority because they constitute memory synchronization events. Also, L1D cache 110 victims go through the full pipeline because, for example, they include updating an internal state in UMC 114. However, a bypass write directly following a victim cache transaction can also be prioritized, ensuring that the bypass write will not be blocked or stalled (analogous to slip-streaming). This prioritized status applies solely to the single bypass write directly following a victim cache transaction, and ends when the bypass write has been sent to the L3 controller 118 for further processing.

Initial scheduling block 202 may have a designated a bypass state (or "bypass mode") in which bypass writes can be scheduled to bypass path 402, rather than to the full memory pipeline 400 (including to a pipeline bank 206). When initial scheduling block 202 is in bypass mode, bypass writes bypass the entire pipeline of an intermediate level of cache, including associated internal arbitration. When initial scheduling block 202 is not in bypass mode, bypass writes go through the full memory pipeline 400.

Figure 5:
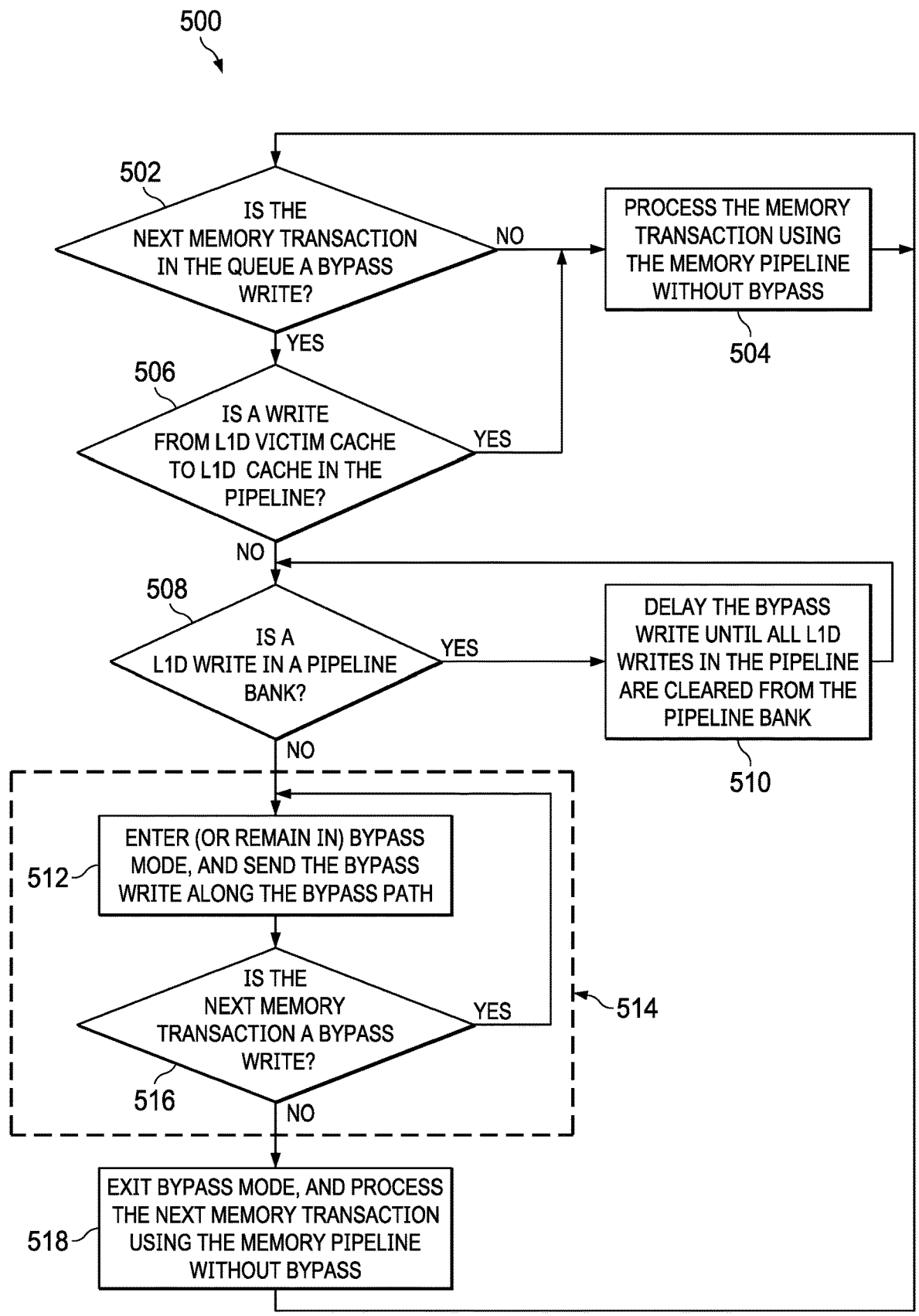
FIG. 5 is an example of a process for memory write operations for the SoC of FIG. 1.

FIG. 5 is an example of a process 500 for memory write operations for SoC 10 of FIG. 1. FIG. 5 describes conditions for initial scheduling block 202 to enter and remain in bypass mode, so that bypass writes are allowed to proceed along the FIG. 4 bypass path 402. In step 502, initial scheduling block 202 determines whether the next memory transaction in the queue is a bypass write, carrying data or relating to a memory location guaranteed not to be written to L2 cache 116. (For example, a data payload too large to fit in the L2 cache 116 or containing a type of data not stored by the L2 cache 116.) If not, then the next memory transaction is processed using normal (non-bypass) processing (goes through the full memory pipeline 400) according to step 504, and the process returns to step 502. In step 506, initial scheduling block 202 determines whether a write to or from L1D victim cache is in the pipeline (in a pipeline bank 206). If so, the victim cache write is prioritized as a memory synchronization event, and in step 504 the bypass write is not allowed to proceed along bypass path 402. Instead, the bypass write receives normal (non-bypass) processing (albeit prioritized non-bypass processing), and process 500 returns to step 502. In step 508, initial scheduling block 202 determines whether there are L1D writes (writes from DMC 104; in some embodiments, any write requests generated outside the memory pipeline 200) in a pipeline bank 206 (the pipeline bank 206 the bypass write would be scheduled to). If so, in step 510, the bypass write is delayed until the L1D writes (all L1D writes in the corresponding pipeline bank 206; in some embodiments, all write requests generated outside the memory pipeline 200) are cleared from respective pipeline banks 206 (for example, respective writes are committed to memory, or reach L3 cache scheduling block 404 for scheduling into a corresponding memory pipeline of the L3 controller 118). Otherwise, in step 512, the bypass write enters bypass mode 514, and the bypass write is sent to L3 controller 118 (and from there to L3 cache 119) along bypass path 402. Next, in step 516, initial scheduling block 202 checks whether the next memory transaction in its queue is a bypass write. If so, process 500 remains in bypass mode by returning to step 512, and the next memory transaction in the queue (a bypass write) is sent to L3 cache scheduling 404 along the bypass path 402. Accordingly, sequentially queued bypass writes after a bypass write has fulfilled conditions to use bypass path 402 can also be sent to L3 cache scheduling 404 via bypass path 402 without having to re-check conditions addressed in steps 506 and 508. If the next memory transaction in the queue of initial scheduling block 202 is not a bypass write, then in step 518 initial scheduling block 202 exits bypass mode, the next memory transaction in the queue receives normal (non-bypass) processing, and the process 500 returns to step 502.

Modifications are possible in the described embodiments, and other embodiments are possible, within the scope of the claims.

In some embodiments, the streaming engine passes on and returns responses for both read and write requests.

In some embodiments, the processor can include multiple processor cores (embodiments with multiple processor cores are not shown), with similar and similarly-functioning couplings to DMC, the streaming engine, and PMC to those shown in and described with respect to FIG. 1.

In some embodiments, bus lines enabling parallel read or write requests can correspond to different types of read or write requests, such as directed at different blocks of memory or made for different purposes.

In some embodiments, the streaming engine enables the processor core to communicate directly with lower level cache (such as L2 cache), skipping higher level cache (such as L1 cache), to avoid data synchronization issues. This can be used to help maintain memory coherence. In some such embodiments, the streaming engine can be configured to transmit only read requests, rather than both read and write requests.

In some embodiments, L3 cache or other lower level memory can schedule write requests so that a write acknowledgment can be sent to DMC (or the processor core or another lower level memory controller) contemporaneously with the write request being scheduled into a corresponding memory pipeline.

In some embodiments, different memory access pipeline banks can have different numbers of stages.

In some embodiments, processors in exterior functions can access data stored in L2 cache; in some such embodiments, coherence between what is stored in L2 cached and what is cached in other processors in exterior functions is not guaranteed.

In some embodiments, writes can be bypass writes if included data is too large for lower level cache (such as L1D cache or L2 cache).

In some embodiments, a write can be a bypass write if a page attribute marks the write as corresponding to a device type memory region that is not cached by UMC (the L2 cache controller).

In some embodiments, L1D cache (or other lower level cache) can cache a data payload of a bypass write.

In some embodiments, memory coherence rules of a processor forbid bypassing memory transactions (memory read requests or memory write requests) other than or in addition to L1D victim cache writes and L1D writes.

In some embodiments, the bypass path jumps a bypass write to a final arbitration stage prior to being scheduled to enter a memory pipeline bank of the L3 cache (not shown).

In some embodiments, a guarantee that a memory write will never be directed to L2 cache (corresponding to a bypass write) includes a guarantee that this this is a choice will never change, or that such a write to L2 cache is impossible.

In some embodiments, a guarantee that a memory write will never be directed to L2 cache includes that L2 cache does not have a copy of, or a hash of, corresponding data.

In some embodiments, a guarantee that a memory write will never be directed to L2 cache can change (be initiated, where the guarantee was not recently in force). In such embodiments, newly making this guarantee (for example, changing a corresponding mode register to make the guarantee) while a line is being written to L2 cache can require that corresponding L2 cache be flushed. A cache flush in this situation avoids a cached copy of a data payload now guaranteed not to be written to L2 cache remaining in L2 cache after the guarantee is made.

In some embodiments, cache controllers only originate memory transactions in response to transactions originated by processor core 102 or exterior functions 120.

In some embodiments, a read or write request can only be scheduled into a corresponding one of pipeline banks 206, depending on, for example, the memory address of the data being written or requested, request load of pipeline banks 206, or a pseudo-random function.

What is claimed is:

1. An integrated circuit device comprising:
a processor core; and
a cache memory hierarchy coupled to the processor core that includes:
a cache memory; and
a cache memory controller circuit coupled to the cache memory that includes:
a memory pipeline associated with the cache memory;
a pipeline bypass path; and
a scheduler circuit coupled to the memory pipeline and the pipeline bypass path and configured to:
receive a write transaction;
determine whether the write transaction specifies a write to the cache memory;
when the write transaction does not specify a write to the cache memory, determine whether an intervening memory transaction inhibits use of the pipeline bypass path; and
provide the write transaction for a subsequent memory via either the memory pipeline or the pipeline bypass path based on whether the write transaction specifies a write to the cache memory and whether the intervening memory transaction inhibits use of the pipeline bypass path.

2. The integrated circuit device of claim 1, wherein the scheduler circuit is configured to determine that the intervening memory transaction inhibits use of the pipeline bypass path based on the intervening memory transaction being associated with a snoop response.

3. The integrated circuit device of claim 1, wherein:
the cache memory is a first cache memory;
the cache memory hierarchy includes a second cache memory arranged between the first cache memory and the processor core; and
the scheduler circuit is configured to determine that the intervening memory transaction inhibits use of the pipeline bypass path based on the intervening memory transaction being associated with memory synchronization of the second cache memory.

4. The integrated circuit device of claim 3, wherein:
the second cache memory includes a victim cache; and
the memory synchronization of the second cache memory is associated with the victim cache.

5. The integrated circuit device of claim 3, wherein:
the first cache memory is an L2 cache memory; and
the second cache memory is an L1 cache memory.

6. The integrated circuit device of claim 3, wherein the scheduler circuit is configured to provide the write transaction for the subsequent memory via the memory pipeline associated with a priority that inhibits blocking and stalling of the write transaction based on the intervening memory transaction being associated with memory synchronization of the second cache memory.

7. The integrated circuit device of claim 1, wherein the scheduler circuit is configured to determine whether the intervening memory transaction delays use of the pipeline bypass path.

8. The integrated circuit device of claim 7, wherein:
the cache memory is a first cache memory;
the cache memory hierarchy includes a second cache memory arranged between the first cache memory and the processor core; and
the scheduler circuit is configured to determine that the intervening memory transaction delays use of the pipeline bypass path when the intervening memory transaction is associated with a write to the second cache memory.

9. The integrated circuit device of claim 8, wherein:
the first cache memory is an L2 cache memory; and
the second cache memory is an L1 cache memory.

10. The integrated circuit device of claim 7, wherein the scheduler circuit is configured to provide the write transaction for the subsequent memory via the pipeline bypass path after the intervening memory transaction completes with respect to the cache memory when the intervening memory transaction delays use of the pipeline bypass path.

11. The integrated circuit device of claim 1, wherein the scheduler circuit is configured to determine that the write transaction does not specify a write to the cache memory based on a payload size of the write transaction.

12. The integrated circuit device of claim 1, wherein the scheduler circuit is configured to determine that the write transaction does not specify a write to the cache memory based on a data type associated with the write transaction.

13. The integrated circuit device of claim 1 further comprising the subsequent memory, wherein:
the cache memory is an L2 cache memory; and
the subsequent memory is an L3 cache memory.

14. An integrated circuit device comprising:
a processor core;
an L1 cache controller coupled to the processor core;
an L1 cache memory coupled to the L1 cache controller;
an L2 cache controller coupled to the L1 cache controller;
an L2 cache memory coupled to the L2 cache controller;
wherein the L2 cache controller includes:
    a memory pipeline associated with the L2 cache memory;
    a pipeline bypass path; and
    a scheduler circuit coupled to the memory pipeline and the pipeline bypass path and configured to:
        receive a write transaction from the L1 cache memory;
        determine whether the write transaction specifies a write to the L2 cache memory;
        when the write transaction does not specify a write to the L2 cache memory, determine whether an intervening memory transaction inhibits servicing the write transaction using the pipeline bypass path; and
        cause the write transaction to be provided to either the memory pipeline or the pipeline bypass path based on whether the write transaction specifies a write to the L2 cache memory and whether the intervening memory transaction inhibits servicing the write transaction using of the pipeline bypass path.

15. The integrated circuit device of claim 14 further comprising an L3 cache controller coupled to the L2 cache controller, wherein the scheduler circuit is further configured to cause the write transaction to be provided to the L3 cache controller via either the memory pipeline or the pipeline bypass path.

16. The integrated circuit device of claim 14, wherein the scheduler circuit is configured to determine that the intervening memory transaction inhibits servicing the write transaction using the pipeline bypass path based on the intervening memory transaction being associated with memory synchronization of the L1 cache memory.

17. A method comprising:
receiving a memory transaction at a cache controller that includes a memory pipeline configured to write to a cache memory and includes a pipeline bypass path;
determining whether the memory transaction is associated with a write to the cache memory;
determining whether a preceding memory transaction inhibits servicing the memory transaction via the pipeline bypass path;
selecting a resource for servicing the memory transaction from among the memory pipeline and the pipeline bypass path based on whether the memory transaction is associated with a write to the cache memory and whether the preceding memory transaction inhibits servicing the memory transaction via the pipeline bypass path; and
servicing the memory transaction via the resource.

18. The method of claim 17, wherein the selecting of the resource is such that the memory transaction is serviced via the memory pipeline when the preceding memory transaction is associated with a snoop response.

19. The method of claim 17, wherein:
the cache memory is a first cache memory; and
the servicing of the memory transaction via the resource includes servicing the memory transaction via the memory pipeline and associated with a priority that inhibits blocking and stalling of the memory transaction based on the preceding memory transaction being associated with memory synchronization of a second cache memory.

20. The method of claim 17 further comprising determining whether the preceding memory transaction delays the servicing of the memory transaction via the pipeline bypass path, wherein the servicing of the memory transaction via the resource includes servicing the memory transaction via the pipeline bypass pass after the preceding memory transaction completes based on the preceding memory transaction delaying the servicing of the memory transaction via the pipeline bypass path.

* * * * *